United States Patent
Squires et al.

(10) Patent No.: US 10,426,204 B2
(45) Date of Patent: Oct. 1, 2019

(54) VENTILATED GARMENT

(71) Applicant: Searah Products, LLC, O'Fallon, MO (US)

(72) Inventors: Gregory A. Squires, St. Peters, MO (US); Lonnie C. Kline, Lake Saint Louis, MO (US); Charles H. Bowen, Dardenne Prairie, MO (US)

(73) Assignee: Searah Products, LLC, O'Fallon, MO (US)

( * ) Notice: Subject to any disclaimer, the term of this patent is extended or adjusted under 35 U.S.C. 154(b) by 176 days.

(21) Appl. No.: 15/609,929

(22) Filed: May 31, 2017

(65) Prior Publication Data

US 2017/0340036 A1 Nov. 30, 2017

Related U.S. Application Data

(60) Provisional application No. 62/343,456, filed on May 31, 2016.

(51) Int. Cl.
*A41D 13/002* (2006.01)
*A61F 5/02* (2006.01)

(52) U.S. Cl.
CPC .......... *A41D 13/0025* (2013.01); *A61F 5/028* (2013.01)

(58) Field of Classification Search
CPC .................................................. A41D 3/0025
USPC ............................................................ 2/102
See application file for complete search history.

(56) References Cited

U.S. PATENT DOCUMENTS

| | | | |
|---|---|---|---|
| 2,171,337 A | 8/1939 | Hellmann et al. | |
| 2,631,290 A | 3/1953 | Klepper | |
| 3,113,320 A | 12/1963 | Cherowbrier et al. | |
| 3,468,299 A | 9/1969 | D'Amato | |
| 4,146,933 A | 4/1979 | Jenkins et al. | |
| 4,998,415 A | 3/1991 | Larsen | |
| 5,564,124 A * | 10/1996 | Elsherif | A41D 13/0025 2/457 |
| 5,970,519 A | 10/1999 | Weber | |
| 6,125,645 A | 10/2000 | Horn | |
| 6,276,155 B2 | 8/2001 | Siman-Tov et al. | |

(Continued)

FOREIGN PATENT DOCUMENTS

CN 202172873 U 3/2012
CN 202385772 U 8/2012

(Continued)

OTHER PUBLICATIONS

Espace English Translation of CN202172873U, 10 pages.

(Continued)

*Primary Examiner* — Katherine M Moran
(74) *Attorney, Agent, or Firm* — Stinson LLP

(57) ABSTRACT

A ventilated garment is configured to be supported on a wearer to provide ventilation to a body part of the wearer. The garment can include an air flow guide that is defined by inner and outer panels. A blower is positioned in the air flow guide to draw air in through an intake and discharge the air through an outlet of the guide. The guide can be arranged on the garment so the intake is adjacent the base of the back of the wearer and the outlet is adjacent the neck. The garment can include a support cushion in operative alignment with the blower to cushion the body part from the blower when the blower is pressed between the body part and a support surface.

17 Claims, 7 Drawing Sheets

(56) References Cited

U.S. PATENT DOCUMENTS

| | | |
|---|---|---|
| 6,295,648 B2 | 10/2001 | Siman-Tov et al. |
| 6,543,247 B2 | 4/2003 | Strauss |
| 6,666,647 B1 | 12/2003 | Trask |
| 6,993,930 B2 | 2/2006 | Blackstone |
| 7,120,938 B2 | 10/2006 | Ichigaya |
| 7,272,946 B2 | 9/2007 | Ichigaya |
| 7,721,349 B1 | 5/2010 | Strauss |
| 8,082,596 B2 | 12/2011 | Pohr et al. |
| 8,306,599 B2 | 11/2012 | Eger |
| 2001/0000849 A1 | 5/2001 | Siman-Tov et al. |
| 2001/0003907 A1 | 6/2001 | Siman-Tov et al. |
| 2004/0083526 A1 | 5/2004 | Ichigaya |
| 2005/0246826 A1 | 11/2005 | McCanter et al. |
| 2006/0080987 A1 | 4/2006 | Ichigaya |
| 2007/0050878 A1 | 3/2007 | Ichigaya |
| 2007/0118956 A1 | 5/2007 | Sawicki et al. |
| 2007/0199124 A1 | 8/2007 | Horn |
| 2007/0271939 A1 | 11/2007 | Ichigaya |
| 2008/0269587 A1 | 10/2008 | Eger |
| 2008/0307567 A1 | 12/2008 | Horn |
| 2010/0242147 A1 | 9/2010 | Pohr et al. |
| 2013/0319031 A1 | 12/2013 | Coats et al. |
| 2017/0089669 A1* | 3/2017 | Levine ............... A41D 13/0025 |

FOREIGN PATENT DOCUMENTS

| | | |
|---|---|---|
| EP | 0490347 A1 | 6/1992 |
| JP | 2006307817 A | 11/2006 |
| WO | 2006009108 A1 | 1/2006 |
| WO | 2008115056 A2 | 9/2008 |
| WO | 2009138713 A1 | 11/2009 |
| WO | 2015011673 A1 | 2/2015 |

OTHER PUBLICATIONS

Espace English Translation of CN202385772U, 9 pages.
Espace English Translation of JP2006307817A, 8 pages.
WIPO English Translation of Description and Claims for WO2006009108A1, 11 pages.

* cited by examiner

VENTILATED GARMENT

CROSS-REFERENCE TO RELATED APPLICATIONS

This application claims the benefit of U.S. Provisional Patent Application Ser. No. 62/343,456, filed May 31, 2016, which is expressly incorporated by reference in its entirety.

FIELD

The present disclosure generally relates to a ventilated garment.

BACKGROUND

Many types of workers operate in hot or humid environments that make it difficult to carry out physical tasks. It is important to keep such workers sufficiently cool as they carry out their work. Maintaining a cool environment at the head and neck can create a sensation of coolness throughout a worker's body.

SUMMARY

In one aspect, a ventilated garment configured to be supported on a back of a wearer comprises an inner panel having a top edge margin, an opposite bottom edge margin, and first and second opposite side edge margins. The inner panel is shaped and arranged for extending vertically along the back of the wearer when the ventilated garment is supported on the back of the wearer such that the bottom edge margin is positioned adjacent a base of the back and the top edge margin is positioned adjacent a neck of the wearer. An outer panel has a top edge margin, an opposite bottom edge margin, and first and second opposite side edge margins. The first and second side edge margins of the outer panel are joined to the first and second side edge margins of the inner panel such that the inner and outer panels define an air flow guide channel therebetween. The bottom edge margins of the inner and outer panels are spaced apart from one another to define an air intake adjacent the base of the back of the wearer in fluid communication with the air flow guide channel, and the top edge margins of the inner and outer panels are spaced apart from one another to define an air flow outlet adjacent the neck of the user in fluid communication with the air flow guide channel. The air flow guide channel fluidly connects the air intake to the air flow outlet. A blower is received in the air flow guide channel and configured to draw air into the air flow guide channel through the air intake and to blow the air vertically through the air flow guide channel and out the air flow outlet thereby providing convective cooling of at least one of the neck and a head of the wearer.

In another aspect, a ventilated garment configured to be supported on a back of a wearer comprises a panel having a top edge margin and an opposite bottom edge margin. The panel is shaped and arranged for extending vertically along the back of the wearer when the ventilated garment is supported on the back of the wearer such that the bottom edge margin is positioned adjacent a lumbar region of the back and the top edge margin is positioned adjacent a neck of the wearer. A blower connected to the ventilated garment adjacent the bottom edge margin of the panel is configured for blowing air vertically along the panel toward to the top edge margin to provide cooling to the wearer. The blower comprises a curved end arranged for supporting the lumbar region of the wearer when the ventilated garment is worn by the wearer and the back of the wearer is supported against a support surface.

In another aspect, a ventilated garment configured to be supported on a body part of a wearer comprises a panel shaped and arranged for extending along the body part when the ventilated garment is supported on the body part of the wearer. A blower is connected to the ventilated garment for blowing air along the panel to provide cooling to the body part. A support cushion is connected to the ventilated garment in operative alignment with the blower to cushion the body part from the blower when the ventilated garment is worn by the wearer and the blower is pressed between the body part and a support surface.

Other aspects and features will be apparent and/or pointed out hereinafter.

BRIEF DESCRIPTION OF THE DRAWINGS

Corresponding reference characters indicate corresponding parts throughout the drawings.

DETAILED DESCRIPTION

Figure 1:
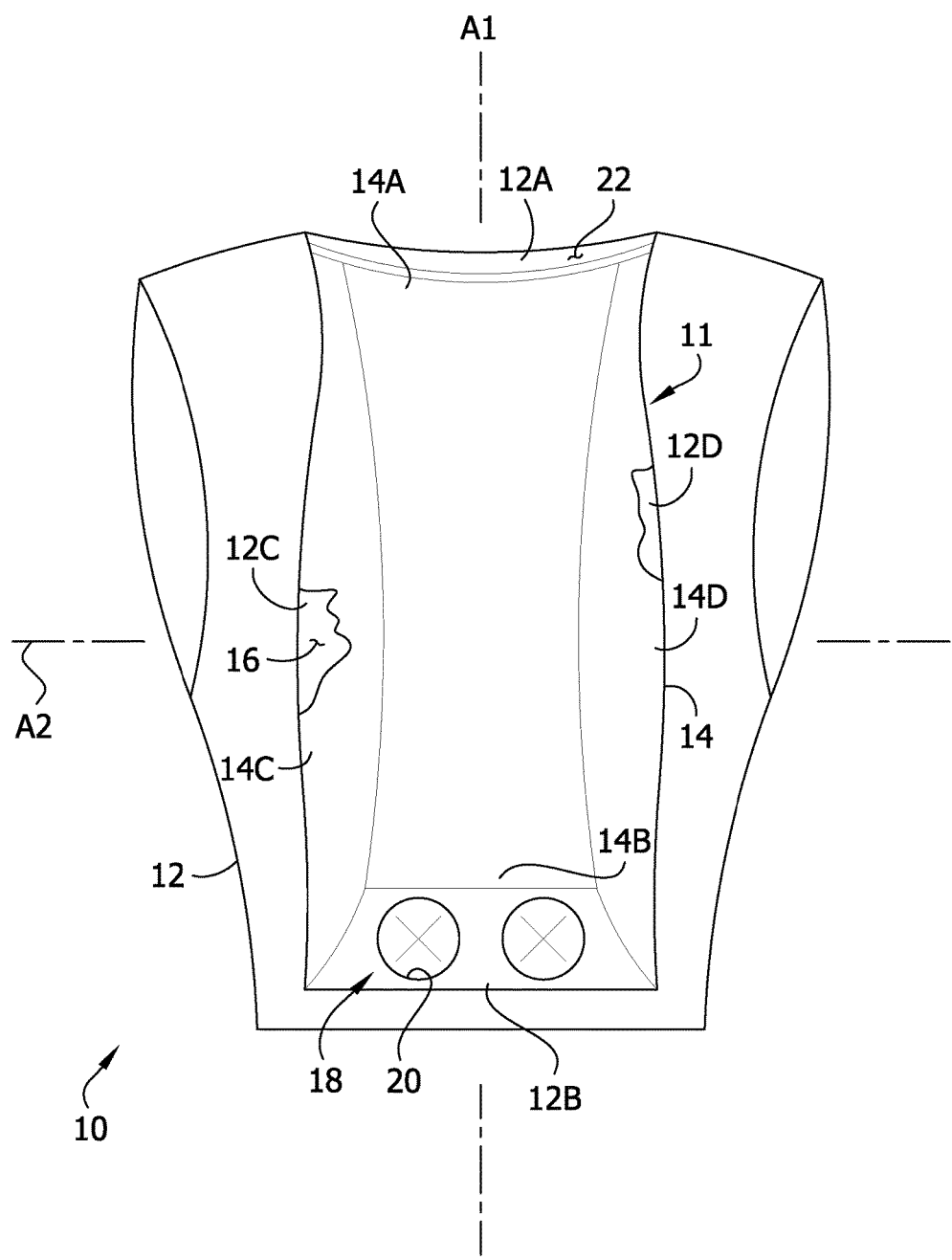
FIG. 1 is a fragmentary rear elevation of a ventilated vest.
Figure 2:
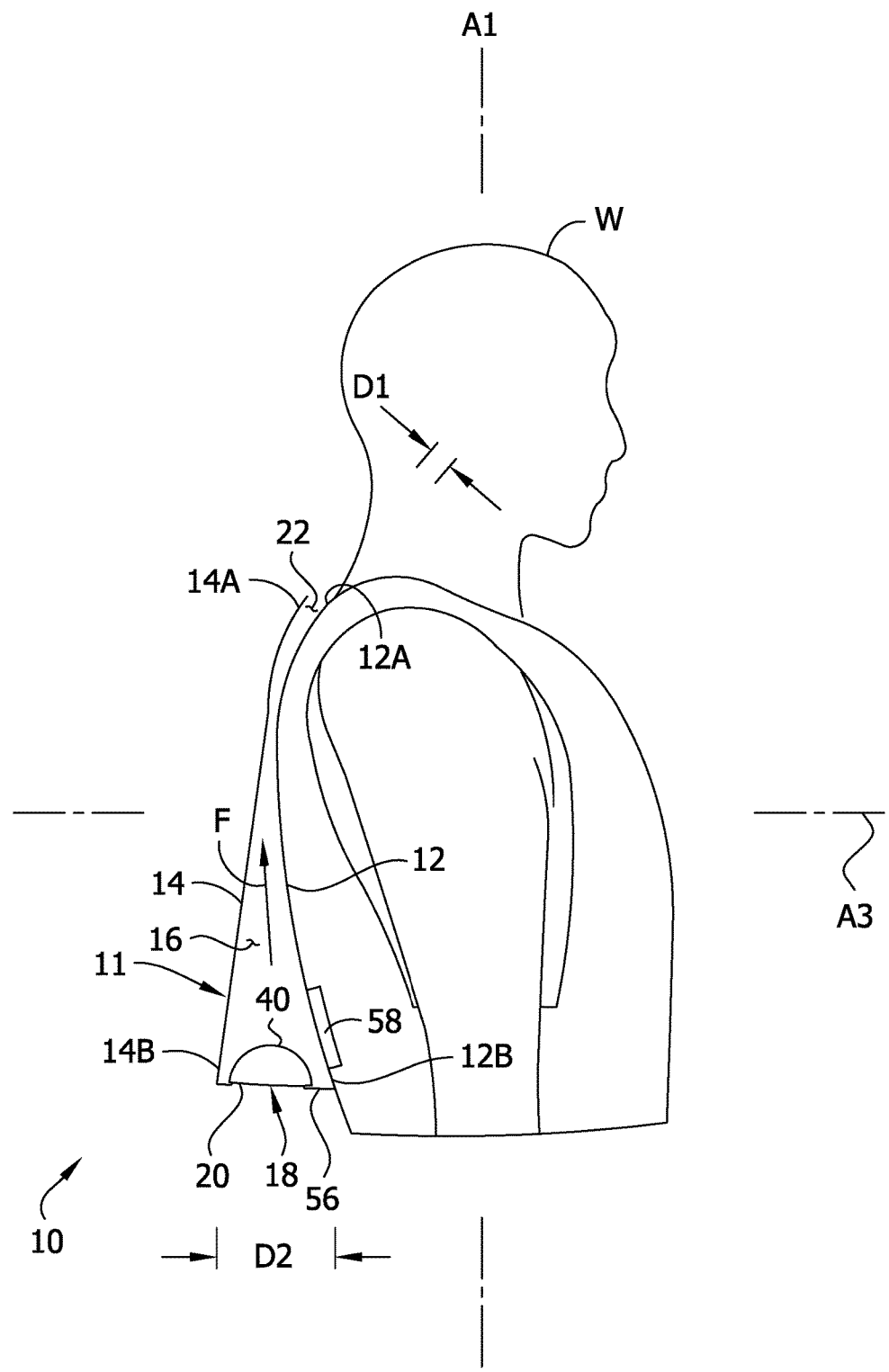
FIG. 2 is a side elevation of the vest illustrating an air flow guide of the vest in cross section.

Referring to FIGS. 1 and 2, a ventilated vest (broadly, a ventilated garment) for being worn by a wearer W is generally indicated at reference number 10. Although the illustrated garment is a vest, it will be understood that other garments configured to be supported on a body part of a wearer W (e.g., shirts, jackets, coats, coveralls, etc.) can be used in other embodiments without departing from the scope of the invention. The vest 10 includes an air flow guide, generally indicated at 11, comprised of inner and outer air flow guide panels 12, 14. The air flow guide 11 defines an air flow guide channel 16 that extends vertically along the back of a wearer W. A blower, generally indicated at 18, is received in the air flow guide channel 16 to blow air vertically through the air flow guide 11 along the back of the wearer W. As will be discussed in further detail below, the inner and outer panels 12, 14 are shaped and arranged to deliver blown air to the head and neck of the wearer W at high velocities to effectively cool these parts of the wearer's body.

The inner panel 12 of the air flow guide 11 comprises a sheet of fabric that extends over the wearer's clothes along the back of the wearer W. In one embodiment, the inner panel 12 comprises an air-permeable fabric to allow some of the air blown through the air flow guide channel 16 to be directed through the inner panel to the back of the wearer W. In another embodiment, the inner panel 12 comprises substantially impermeable fabric to maximize air flow to the head and neck of the wearer W and limit losses in air flow energy along the back of the wearer. The inner panel 12 has a top edge margin 12A and a bottom edge margin 12B spaced apart from one another along a vertical axis A1. The inner panel 12 also includes a first side edge margin 12C and an opposite second side edge margin 12D spaced apart from one another along a lateral axis A2. The inner panel 12 is preferably shaped and arranged so that, when the vest 10 is worn by the wearer W, the top edge margin 12A is located adjacent the head and/or neck of the wearer and the bottom edge margin 12B is located adjacent a base of the back of the wearer. The side edge margins 12C, 12D can be positioned adjacent the sides of the back of the wearer W in use.

The outer panel 14 of the air flow guide 11 comprises a sheet of substantially air-impermeable fabric to limit air flow losses in directions away from the wearer along the air flow guide. The outer panel 14 has a top edge margin 14A and a bottom edge margin 14B spaced apart from one another along the vertical axis A1. The outer panel 14 also includes a first side edge margin 14C and an opposite second side edge margin 14D spaced apart from one another along the lateral axis A2. In the illustrated embodiment, the outer panel 14 is shaped and arranged so that, when the vest 10 is worn by the wearer W, the top edge margin 14A is located adjacent the top edge margin 12A of the inner panel the inner panel 12 along the vertical axis A1. Thus, the top edge margin 14A is generally vertically aligned with a base of the head of the wearer W. The bottom edge margin 14B is located at a base of the back of the wearer, in general vertical alignment with the bottom edge margin 12B of the inner panel. The side edge margins 14C, 14D are laterally aligned with the side edge margins 12C, 12D along the lateral axis A2, adjacent the sides of the back of the wearer.

The side edge margins 14C, 14D of the outer panel 14 are joined to the side edge margins 12C, 12D of the inner panel and a laterally central portion of the outer panel is spaced apart from the inner panel along a transverse axis A3 to define the air flow guide channel 16. The bottom edge margins 12B, 14B are spaced apart from one another along the transverse axis A3 to define an air intake 20 adjacent the base of the back of the wearer W. Likewise, the top edge margins 12A, 14A are spaced apart from one another along the transverse axis A3 to define an air flow outlet 22 adjacent the neck of the wearer W. The air intake 20 and air flow outlet 22 are each in fluid communication with the air flow guide channel 16. The air flow guide channel 16, therefore, fluidly connects the air intake 20 to the air flow outlet 22. The blower 18 is configured to draw air into the air flow guide channel 16 through the air flow intake 20 and blow the air through the air flow guide channel and out the air flow outlet 22 to cool the head and neck of the wearer W. In embodiments in which the inner panel 12 comprises air-permeable fabric, some of the blown air flows through pores or openings in the inner panel to cool the back of the wearer W. In embodiments in which the inner panel 12 comprises air-impermeable fabric, substantially all of the blown air is directed to the neck and head of the wearer W. The illustrated air flow guide 11 defines a single channel 16 between the intake 20 and outlet 22 that conveys all of the air blown by the blower 18. Other air flow guides can define multiple flow channels without departing from the scope of the invention.

The inner and outer panels 12, 14 are shaped and arranged to direct a high velocity air stream toward the head and neck of the wearer W. As shown in FIGS. 1 and 2, at the top and bottom edge margins 14A, 14B, the outer panel 14 has a generally convex shape that protrudes outwardly from the inner panel 12. The top and bottom edge margins 14A, 14B respectively extend from the first side edge margin 14C to a respective apex and from the apex to the second side edge margin 14D. The top apex is spaced apart from the top edge margin 12A of the inner panel 12 along the transverse axis A3 by a distance D1, and the bottom apex 38 is spaced apart from the bottom edge margin 12A of the inner panel along the transverse axis by a distance D2. The distance D2 is greater than the distance D1, such as between 1.5 and 3 times greater, for example.

Thus, as compared with bottom edge margin 14B, the top edge margin 14A of the outer panel 14 has a more flattened shape and defines a constricted region of the air flow guide channel 16. The air flow guide channel 16 thus has a cross-sectional shape transverse to the vertical axis A1 that decreases in size as the outer panel 14 extends upward along the vertical axis A1 from adjacent the bottom edge margin 14B toward the constricted region adjacent the top edge margin 14A. For example, the outer panel 14 has a central portion between the first and second side edge margins 14C, 14D that angles inward toward the inner panel as it extends from the bottom edge margin 14B toward the top edge margin 14A. The cross-sectional shape of the air flow guide channel 16 has a minimum constricted size at the air flow outlet 22 in the illustrated embodiment, and thus the air flow outlet is constricted in size with respect to the air intake 20. As explained below, air is blown through the air flow guide channel 16 generally along the vertical axis A1. The blown air flows through a lower region the air flow guide channel 16 at a first velocity and accelerates as the lower region narrows toward the constricted air flow outlet 22. The constriction in cross-sectional shape of the air flow guide channel 16 accelerates the air flow so that the air flow has a higher velocity as it exits the outlet 22. The accelerated air flow is discharged through the outlet 22 toward the head and neck of the wearer W once it passes through the constricted region. As a result, the head and neck region of the wearer W receive a powerful stream of blown air that convectively cools the wearer W.

Figure 4:
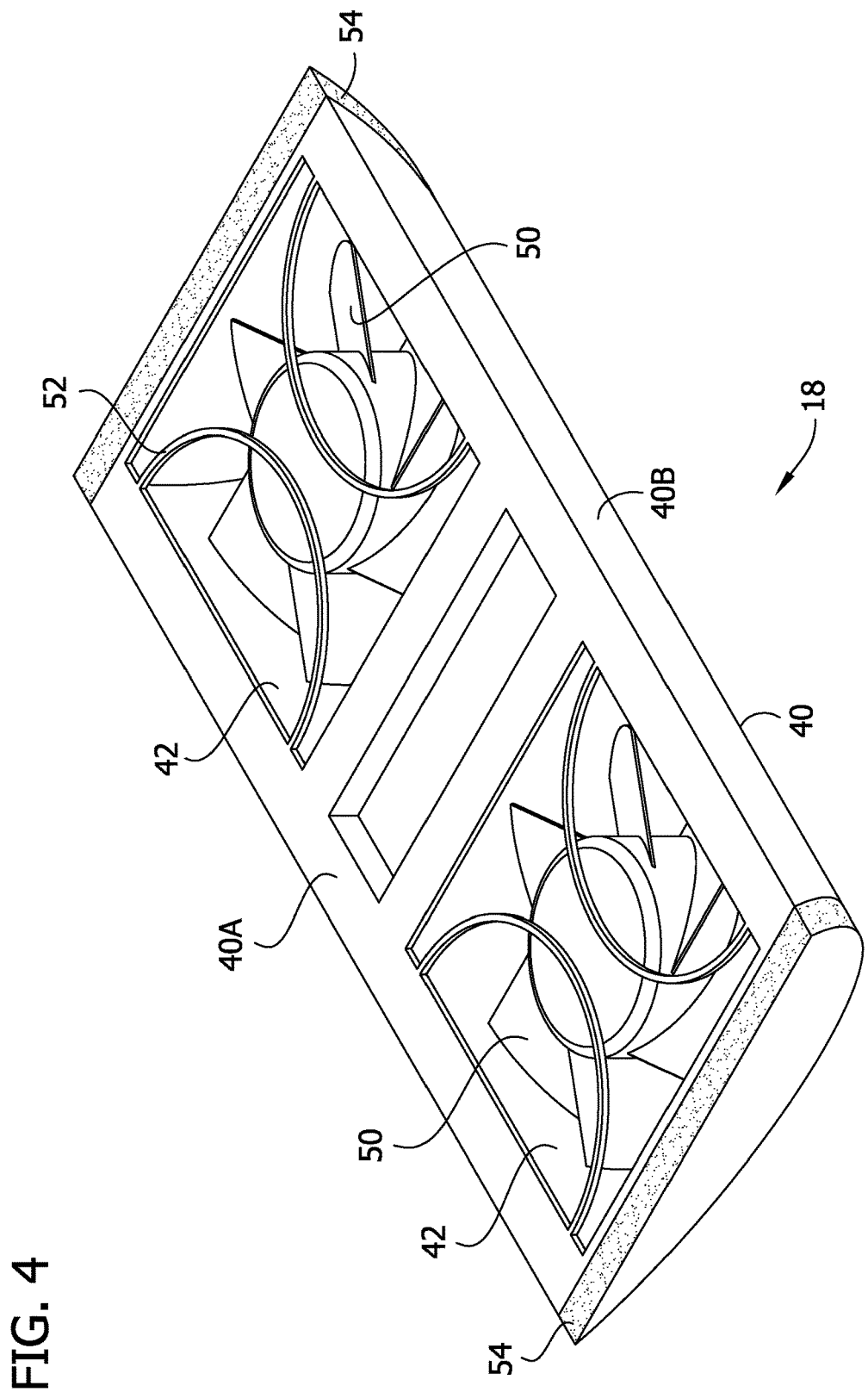
FIG. 4 is an upstream perspective of a blower of the vest.
Figure 5:
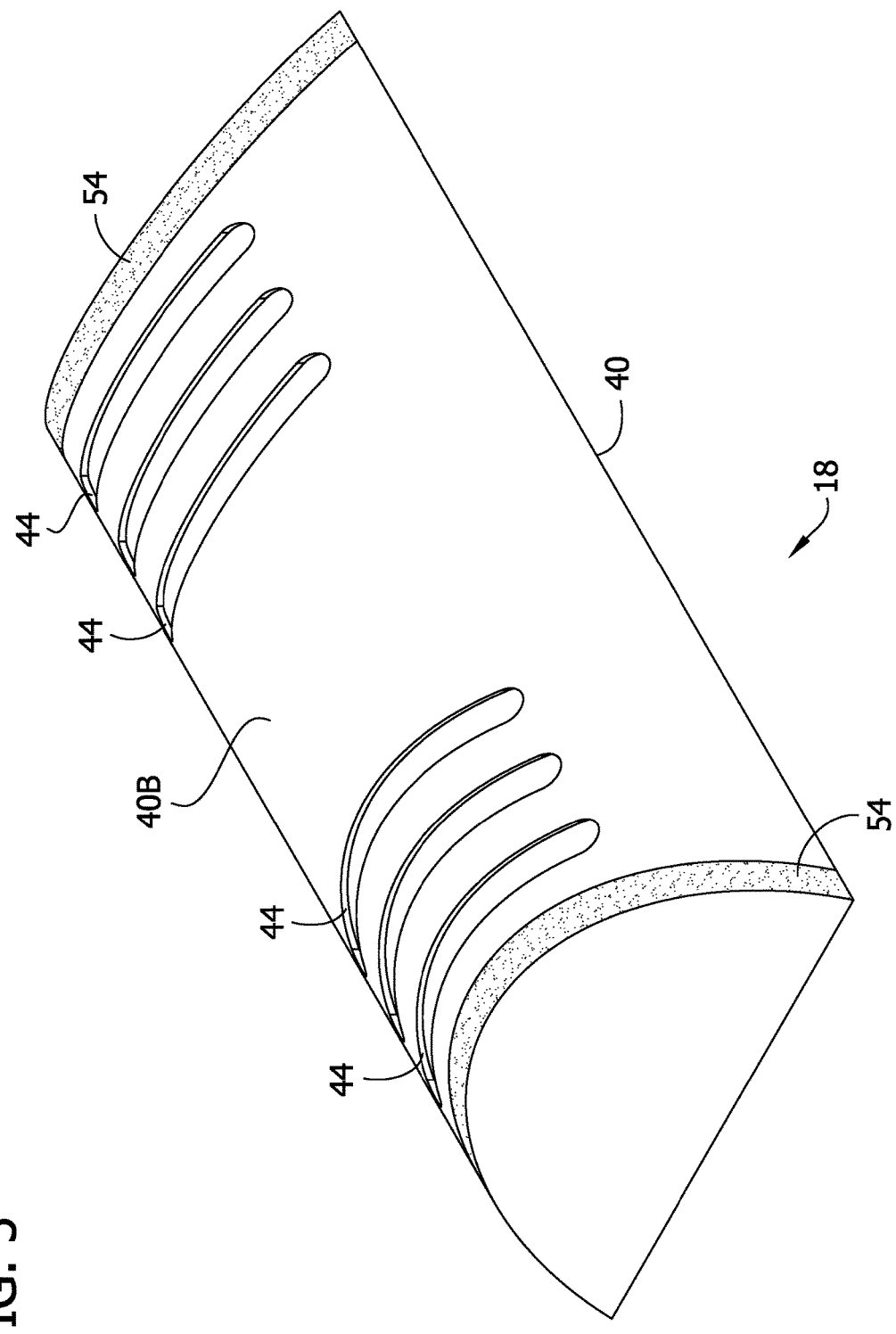
FIG. 5 is a downstream perspective of the blower.

As shown in FIGS. 4 and 5, the blower 18 comprises a rigid or semi-rigid fan enclosure 40 and two fans 50. The blower 18 is configured to be positioned within the air flow guide channel 16 adjacent the air intake 20. It will be understood that the blower can include any suitable number of fans without departing from the scope of the invention. Moreover, blowers other than fans could also be used without departing from the scope of the invention. The fan enclosure 40 has a substantially flat upstream end 40A and a curved downstream end 40B. In use, the enclosure 40 is positioned in the air flow guide channel 16 such that the upstream end 40A is positioned adjacent the bottom air intake 20. The fan enclosure 40 defines an interior fan chamber sized and arranged for receiving the fans 50 and a power supply (e.g., battery, not shown) for powering the fans. The upstream end 40A of the enclosure 40 defines intake openings 42 spaced apart along the lateral axis A2 in operative alignment with the fans 50. The intake openings 42 fluidly communicate with the interior of the enclosure 40 so that the fans 50 can draw air into the fan enclosure through the intake openings. Grills 52 are secured to the upstream end 40A over the openings 42 in the illustrated embodiment. The downstream end 40B of the enclosure 40 defines outlet openings 44 in operative alignment with the fans 50. The outlet openings 44 fluidly communicate with the interior of the enclosure 40 and can have any configuration suitable for discharging air blown by the fans 50 into the air flow guide channel 16 in use.

Referring to FIG. 2, the blower 18 is positioned between the bottom edge margin 12B of the inner panel 12 and the bottom edge margin 14B of the outer panel 14. When installed in the air flow guide 11, the blower 18 holds the bottom edge margin 14B of the outer panel 14 in spaced apart relationship with the bottom edge margin 12B of the inner panel 12 without the need for any separate rigid framing in the air flow guide. In other embodiments, the outer panel could be held in position by, for example, a wire frame. As shown in FIGS. 4 and 5, a hook and loop fastener strap 54 is secured around each end portion of the fan enclosure 40. The hook and loop fastener straps 54 are configured to engage mating hook and loop material attached to the air flow guide 11 to secure the blower 18 in place with respect to the air flow guide. As shown in FIG. 2, the illustrated air flow guide 11 includes a bottom panel 56 extending between the bottom edge margin 12B of the inner panel 12 and the bottom edge margin 14B of the outer panel 14 that supports hook and loop material configured for mating with the hook and loop straps 54. Suitably, the bottom panel 56 includes one or more air flow openings defining the air intake 20 to permit the blower 18 to draw air into the air flow guide channel 16 through the air flow openings 42. In one or more embodiments, at least a portion of the bottom panel 56 can be selectively separated from the air flow guide 11 to allow the blower 18 to be removed. It is understood that the blower could be connected to the air flow guide in other ways in other embodiments.

The fans 50 are oriented to blow air vertically through the air flow guide channel 16 along an air flow path F (FIG. 2). In the illustrated embodiment, the fans 50 are configured to rotate fan blades about respective axes of rotation oriented generally parallel to the vertical axis A1 to blow air along the flow path F. In use, the fans 50 rotate the fan blades 52 about their axes of rotation to draw air through the intake 20. The fans can be selectively controlled by a user inter face (e.g., a switch accessible to the wearer W, not shown). The fans 50 direct the air along the flow path F, and the air accelerates as the air flow guide channel 16 narrows. The accelerated air flow F is discharged through the air flow outlet 22 at a relatively high velocity (e.g., a higher velocity than at the outlet openings 54 of the fans 50). The high velocity air flow cools the head and neck of the wearer W as it flows out of the outlet 22.

Figure 3:
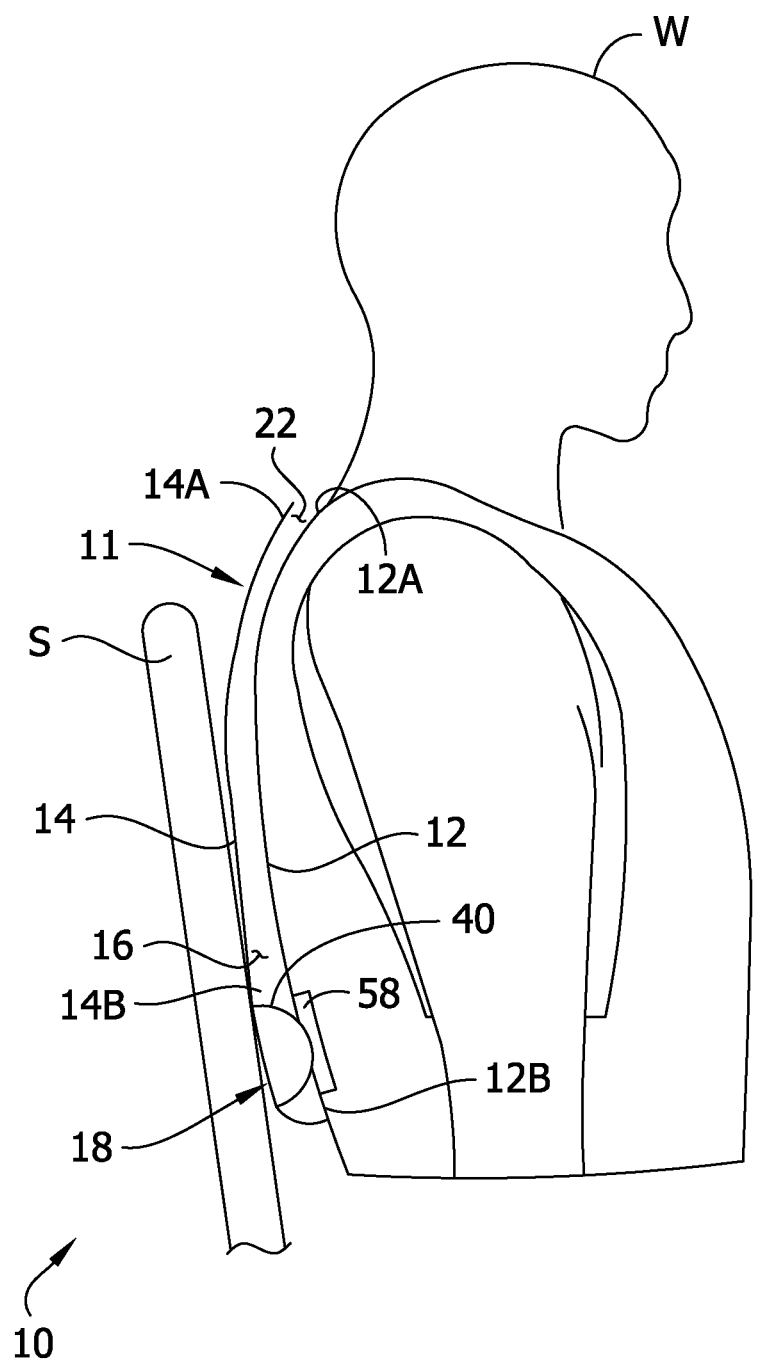
FIG. 3 is a side elevation similar to FIG. 2, illustrating the air flow guide supported against a back support.

Referring to FIG. 3, when the back of the wearer W is rested against a back support S, the vest 10 is configured to provide cushioned lumbar support. As discussed above, the downstream end 40B of the fan enclosure 40 is curved. As shown in FIG. 3, the downstream end 40B is operatively aligned with a support cushion 58. In one or more embodiments, the cushion 58 is received in a pouch that is attached to the inner panel 12 adjacent the bottom end portion 12 thereof. When the back of the wearer W is supported against the support S, the curved downstream end 40B of the fan enclosure 40 presses the cushion 58 against the lumbar region of the back to provide cushioned support. That is, when the back of the wearer W engages the back support the curved end 40B rolls up along the lumbar region of the back and presses against the cushion 58 to provide lumbar support. Thus, the support cushion 58 is connected to the ventilated vest 10 for being received between the curved end 40B of the blower enclosure 40 and the lumbar region of the wearer W, and the vest can be worn comfortably while the back of the wearer is supported against a back support S such as the back of a chair without removing the blower 18 from the vest.

As can be seen, the illustrated vest 10 provides convective cooling of the head and neck of the wearer W. The vest 10 uses a suitably shaped air flow guide 11 to deliver a high velocity air stream F to the head and neck for effective cooling. The vest 10 can be worn comfortably, for example, by a worker in a hot or humid environment, as an outer garment, over the clothes of the wearer W without interfering with normal workplace activities such as sitting in a chair. A plurality of the vests 10 can be stored at or transported to a work site, where they can be distributed to workers on an as needed basis. The vests 10 can be folded and stored in a space-efficient manner when not in use. Thus, it can be seen, that the vest 10 provides an easy-to-implement cooling solution that can be distributed and utilized on an as-needed basis.

Figure 6:
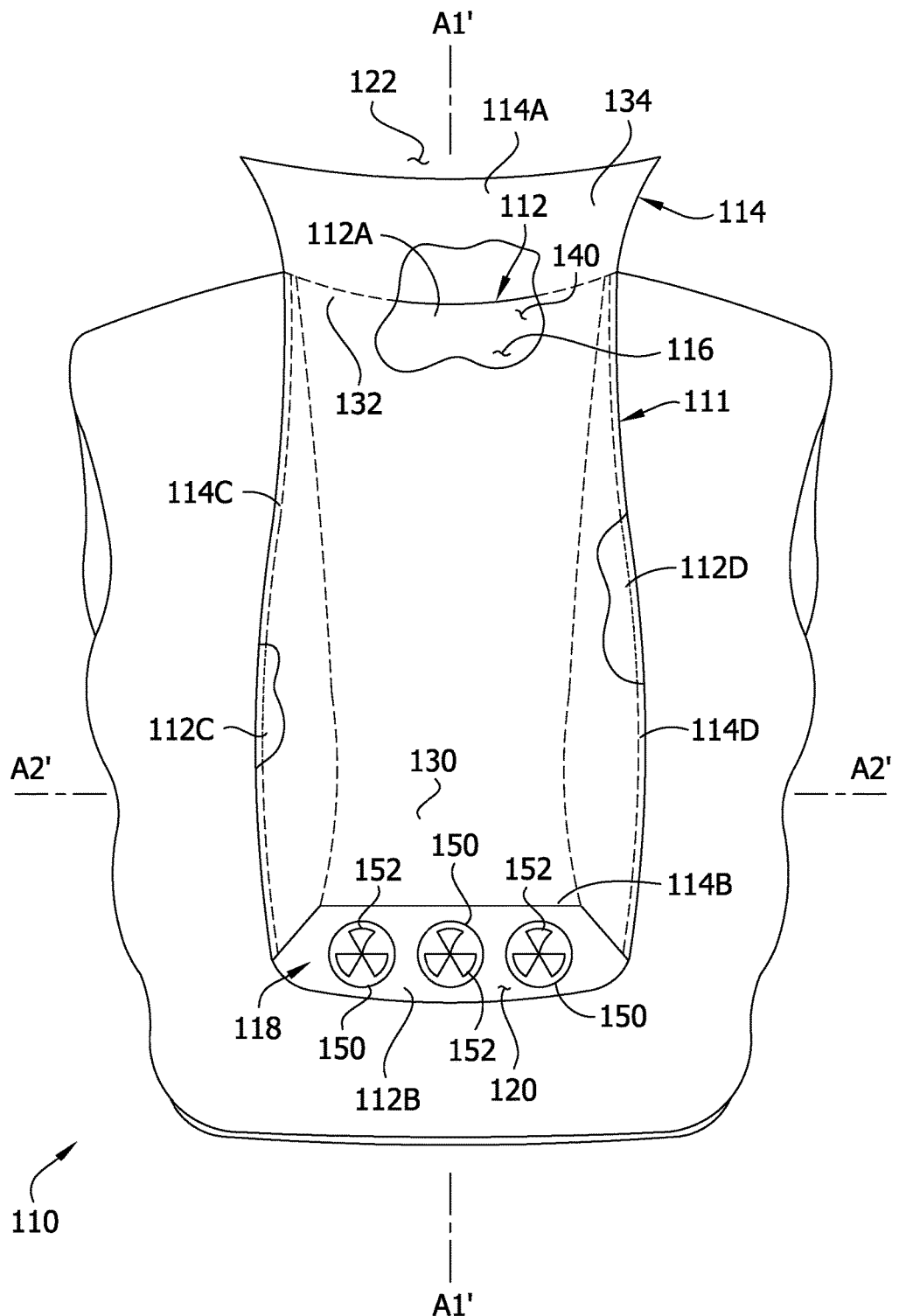
FIG. 6 is a fragmentary rear elevation of another ventilated vest.

Referring to FIGS. 5 and 6, another embodiment of a ventilated vest is generally indicated at reference number 110. The vest 110 includes an air flow guide, generally indicated at 111, comprised of inner and outer air flow guide panels 112, 114. The air flow guide 111 defines an air flow guide channel 116 that extends vertically along the back of the wearer W. A blower, generally indicated at 118, is received in the air flow guide channel 116 to blow air vertically through the air flow guide 111 along the back of the wearer W. The inner and outer panels 112, 114 are shaped and arranged to deliver blown air to the head and neck of the wearer W at high velocities to effectively cool these parts of the wearer's body.

In the illustrated embodiment, the inner panel 112 of the air flow guide 111 comprises a sheet of air-impermeable fabric that extends over the wearer's clothes along the back of the wearer W. The inner panel 112 has a top edge margin 112A and a bottom edge margin 112B spaced apart from one another along a vertical axis A1'. The inner panel 112 also includes a first side edge margin 112C and an opposite second side edge margin 112D spaced apart from one another along a lateral axis A2'. The inner panel 112 is preferably shaped and arranged so that, when the vest 110 is worn by the wearer W, the top edge margin 112A is located at a base of the neck of the wearer and the bottom edge margin 112B is located at a base of the back of the wearer. The side edge margins 112C, 112D are preferably positioned adjacent the sides of the back of the wearer W in use.

Like the inner panel 112, the outer panel 114 of the air flow guide 111 preferably comprises a sheet of substantially air-impermeable fabric. But unlike the inner panel 112, the outer panel 114 is spaced apart from the back of the wearer W along its height. The outer panel 114 has a top edge margin 114A and a bottom edge margin 114B spaced apart from one another along the vertical axis A1'. The outer panel 114 also includes a first side edge margin 114C and an opposite second side edge margin 114D spaced apart from one another along the lateral axis A2'. The outer panel 114 is preferably shaped and arranged so that, when the vest 110 is worn by the wearer W, the top edge margin 114A is spaced apart from the top edge margin 112A of the inner panel 112 along the vertical axis A1'. A suitable framework (e.g., a wire framework, etc.) can shape and support the outer panel 114 in the desired configuration. In the illustrated embodiment, the top edge margin 114A is generally vertically aligned with a base of the head of the wearer W. The bottom edge margin 114B is located at a base of the back of the wearer, in vertical alignment with the bottom edge margin 112B. The side edge margins 114C, 114D are laterally aligned with the side edge margins 112C, 112D along the lateral axis A2', adjacent the sides of the back of the wearer.

The side edge margins 114C, 114D of the outer panel 114 are joined to the side edge margins 112C, 112D of the inner panel and laterally central portions of the outer panel are spaced apart from the inner panel along a transverse axis A3' to define the air flow guide channel 116. The bottom edge margins 112B, 114B are spaced apart from one another along the transverse axis A3' to define an air intake 120 adjacent the base of the back of the wearer W. Likewise, the top edge margins 112A, 114A are spaced apart from one another along the transverse axis A3' to define an air flow outlet 122 adjacent the neck of the user. The air intake 120 and air flow outlet 122 are each in fluid communication with the air flow guide channel 116. The air flow guide channel 116, therefore, fluidly connects the air intake 120 to the air flow outlet 122. Because the panels 112, 114 comprise substantially air impermeable fabric, substantially all of the cooling air flow is directed to the head and neck of the wearer W, as opposed to being dispersed along the back of the wearer. Of course, it is understood that an air-permeable fabric could be used for the inner panel 114 if cooling air flow along the back of the wearer W is desired. The illustrated air flow guide 111 defines a single channel 116 between the intake 120 and outlet 122 that conveys substantially all of the air blown by the blower 118. Other air flow guides can define multiple flow channels without departing from the scope of the invention.

The inner and outer panels 112, 114 are shaped and arranged to direct a high velocity air stream toward the head and neck of the wearer W. As shown best in FIG. 7, the illustrated outer panel 114 has a half-hourglass shape. The outer panel 114 comprises a relatively wide (along the transverse axis A3') bottom end portion 130, a central constricted portion 132, and a relatively wide top end portion 134. The central constricted portion 132 is spaced apart between the top and bottom edge margins 114A, 114B along the vertical axis A1'. The central constricted portion 132 is located closer to the top edge margin 114A than to the bottom edge margin 114B. In the illustrated embodiment, the central constricted portion 132 is located adjacent top ends of shoulder blades of the wearer W when the ventilated garment is supported on the back of the wearer. The bottom end portion 130 extends from the bottom edge margin 114B upward to the central constricted portion 132, and the top end portion 134 extends from the central constricted portion upward to the top edge margin 114A. The bottom end portion 130 angles inward toward the inner panel 112 along the transverse axis A3' as it extends upward from the bottom edge margin 114B. The top end portion 134 angles outward away from the inner panel 112 along the transverse axis A3' as it extends upward from the central constricted portion 132.

Figure 7:
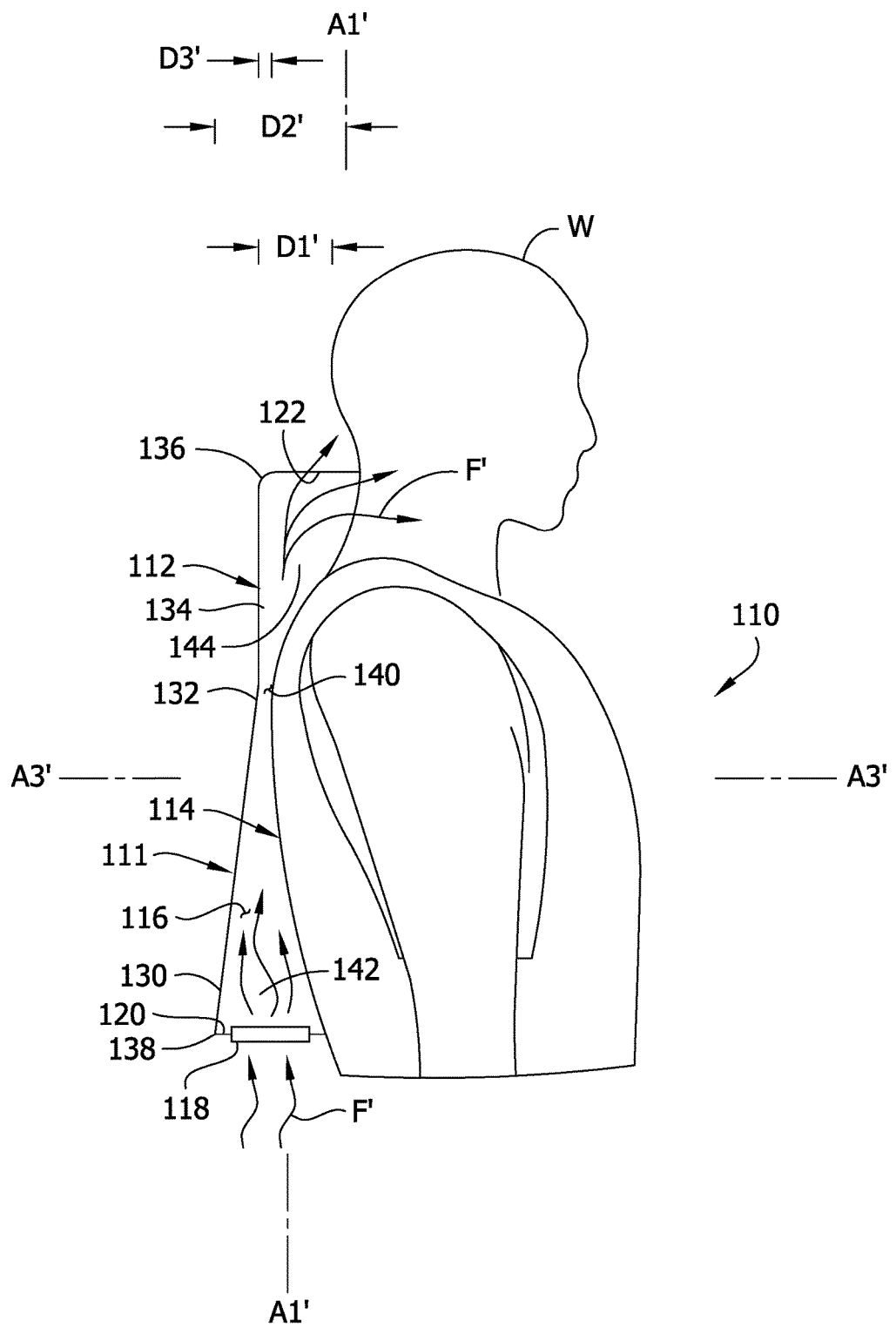
FIG. 7 is a side elevation of the vest of FIG. 6, illustrating an air flow guide of the vest in cross section.

As shown in FIGS. 6 and 7, at the top and bottom edge margins 114A, 114B, the top and bottom end portions 130, 134 each have a generally convex shape. The top and bottom edge margins 114A, 114B respectively extend from the first side edge margin 114C to a respective apex 136, 138, and from the apex to the second side edge margin 114D. The top apex 136 is spaced apart from the top edge margin 112A of the inner panel 112 along the transverse axis A3' by a distance D1, and the bottom apex 38 is spaced apart from the bottom edge margin 112A of the inner panel along the transverse axis A3' by a distance D2'. The distance D2' is greater than the distance D1', such as between 1.5 and 3 times greater.

As compared with the top and bottom edge margins 114A, 114B, the central constricted portion 132 of the outer panel 114 has a more flattened shape. The central constricted portion 132 extends from adjacent the first side edge margin 114C toward the second side edge margin 114D. As it extends between the first and second side edge margins 114C, 114D, the central constricted portion 132 is spaced apart from the first side panel 112 along the transverse axis A3' by no more than a third distance D3', which is considerably shorter than the first and second distances D1', D2'.

The central constricted portion 132 of the outer panel 114 defines a constricted region 140 of the air flow guide channel 116. Air flows through the air flow guide channel 116 generally along the vertical axis A1'. The blown air flows through a lower region 142 of the air flow guide channel 116 at a first velocity and accelerates as the lower region narrows toward the constricted region 140. The constricted region 140 accelerates the air flow so that the air flow has a higher velocity as it exits the constricted region 140 and passes into an upper region 144. Because the top edge margin 112A of the inner panel 112 is positioned lower than the top edge margin 114A of the outer panel, the accelerated air flow is almost immediately discharged through the outlet 122 toward the head and neck of the wearer W once it passes through the constricted region 140. As a result, the head and neck region of the wearer W receive a powerful stream of blown air that convectively cools the wearer W.

As shown in FIG. 6, the illustrated blower 118 comprises three fans 150 positioned within the air flow guide channel 116 at the air intake 120. The fans 150 are mounted in the air flow guide 111 at the base of the back of the wearer W. The fans 50 are positioned between the bottom edge margin 112B of the inner panel 112 and the bottom edge margin 112C of the outer panel 114. The fans 150 are oriented to blow air vertically through the air flow guide channel 116 along an air flow path F'. Each fan 150 comprises a corresponding fan blade 152. The fans 150 are configured to rotate the fan blades 152 about respective axes of rotation oriented generally parallel to the vertical axis A1' to blow air along the flow path F'.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products without departing from the scope of the invention, it is intended that all matter contained in the above description and shown in the accompanying drawings shall be interpreted as illustrative and not in a limiting sense.

What is claimed is:

1. A ventilated garment configured to be supported on a back of a wearer, the ventilated garment comprising:
   an inner panel having a top edge margin, an opposite bottom edge margin, and first and second opposite side edge margins, the inner panel being shaped and arranged for extending vertically along the back of the wearer when the ventilated garment is supported on the back of the wearer such that the bottom edge margin is positioned adjacent a base of the back and the top edge margin is positioned adjacent a neck of the wearer;
   an outer panel having a top edge margin, an opposite bottom edge margin, and first and second opposite side edge margins, the first and second side edge margins of the outer panel being joined to the first and second side edge margins of the inner panel such that the inner and outer panels define an air flow guide channel therebetween, the bottom edge margins of the inner and outer panels being spaced apart from one another to define an air intake adjacent the base of the back of the wearer in fluid communication with the air flow guide channel and the top edge margins of the inner and outer panels being spaced apart from one another to define an air flow outlet adjacent the neck of the user in fluid communication with the air flow guide channel, the air flow guide channel fluidly connecting the air intake to the air flow outlet; and a blower received in the air flow guide channel and configured to draw air into the air flow guide channel through the air intake and to blow the air vertically through the air flow guide channel and out the air flow outlet thereby providing convective cooling of at least one of the neck and a head of the wearer;

wherein the bottom edge margin and the top edge margin of the outer panel each have a generally convex shape.

2. A ventilated garment as set forth in claim 1 wherein the ventilated garment comprises a vest.

3. A ventilated garment configured to be supported on a back of a wearer, the ventilated garment comprising:

an inner panel having a top edge margin, an opposite bottom edge margin, and first and second opposite side edge margins, the inner panel being shaped and arranged for extending vertically along the back of the wearer when the ventilated garment is supported on the back of the wearer such that the bottom edge margin is positioned adjacent a base of the back and the top edge margin is positioned adjacent a neck of the wearer;

an outer panel having a top edge margin, an opposite bottom edge margin, and first and second opposite side edge margins, the first and second side edge margins of the outer panel being joined to the first and second side edge margins of the inner panel such that the inner and outer panels define an air flow guide channel therebetween, the bottom edge margins of the inner and outer panels being spaced apart from one another to define an air intake adjacent the base of the back of the wearer in fluid communication with the air flow guide channel and the top edge margins of the inner and outer panels being spaced apart from one another to define an air flow outlet adjacent the neck of the user in fluid communication with the air flow guide channel, the air flow guide channel fluidly connecting the air intake to the air flow outlet; and a blower received in the air flow guide channel and configured to draw air into the air flow guide channel through the air intake and to blow the air vertically through the air flow guide channel and out the air flow outlet thereby providing convective cooling of at least one of the neck and a head of the wearer;

wherein the outer panel has a central portion between the first and second side edge margins thereof that angles inward toward the inner panel as it extends from the bottom edge margin toward the top edge margin of the outer panel.

4. A ventilated garment as set forth in claim 3 wherein the air flow outlet is constricted in size with respect to the air intake.

5. A ventilated garment as set forth in claim 3 wherein the outer panel comprises substantially air-impermeable fabric.

6. A ventilated garment as set forth in claim 3 wherein the top edge margins of the inner and outer panels are located adjacent a base of the neck of the wearer when the ventilated garment is supported on the back of the wearer.

7. A ventilated garment as set forth in claim 3 wherein the blower is located adjacent the bottom end margins of the inner and outer panels.

8. A ventilated garment as set forth in claim 3 wherein the blower comprises a fan enclosure defining an interior chamber and at least one at least one fan received in the interior chamber of the fan enclosure.

9. A ventilated garment as set forth in claim 8 wherein the fan enclosure is configured to hold the outer panel in spaced apart relationship with the inner panel.

10. A ventilated garment as set forth in claim 8 wherein the fan enclosure has an upstream end defining an intake opening in fluid communication with the interior chamber and a downstream end defining an outlet opening in fluid communication with the interior chamber, the fan being configured to draw air into the interior chamber through the intake opening and to discharge air into the air flow channel through the outlet opening.

11. A ventilated garment configured to be supported on a back of a wearer, the ventilated garment comprising:

an inner panel having a top edge margin, an opposite bottom edge margin, and first and second opposite side edge margins, the inner panel being shaped and arranged for extending vertically along the back of the wearer when the ventilated garment is supported on the back of the wearer such that the bottom edge margin is positioned adjacent a base of the back and the top edge margin is positioned adjacent a neck of the wearer;

an outer panel having a top edge margin, an opposite bottom edge margin, and first and second opposite side edge margins, the first and second side edge margins of the outer panel being joined to the first and second side edge margins of the inner panel such that the inner and outer panels define an air flow guide channel therebetween, the bottom edge margins of the inner and outer panels being spaced apart from one another to define an air intake adjacent the base of the back of the wearer in fluid communication with the air flow guide channel and the top edge margins of the inner and outer panels being spaced apart from one another to define an air flow outlet adjacent the neck of the user in fluid communication with the air flow guide channel, the air flow guide channel fluidly connecting the air intake to the air flow outlet; and a blower received in the air flow guide channel and configured to draw air into the air flow guide channel through the air intake and to blow the air vertically through the air flow guide channel and out the air flow outlet thereby providing convective cooling of at least one of the neck and a head of the wearer;

wherein the air flow channel has a cross-sectional shape transverse to the vertical axis, the cross-sectional shape decreasing in size as the outer panel extends along the vertical axis from the bottom edge margin toward the top edge margin.

12. A ventilated garment as set forth in claim 11 wherein the cross-sectional shape of the air flow channel has a minimum constricted size at the air flow outlet.

13. A ventilated garment configured to be supported on a back of a wearer, the ventilated garment comprising:

an inner panel having a top edge margin, an opposite bottom edge margin, and first and second opposite side edge margins, the inner panel being shaped and arranged for extending vertically along the back of the wearer when the ventilated garment is supported on the back of the wearer such that the bottom edge margin is positioned adjacent a base of the back and the top edge margin is positioned adjacent a neck of the wearer;

an outer panel having a top edge margin, an opposite bottom edge margin, and first and second opposite side edge margins, the first and second side edge margins of the outer panel being joined to the first and second side edge margins of the inner panel such that the inner and outer panels define an air flow guide channel therebetween, the bottom edge margins of the inner and outer panels being spaced apart from one another to define an air intake adjacent the base of the back of the wearer in fluid communication with the air flow guide channel and the top edge margins of the inner and outer panels being spaced apart from one another to define an air flow outlet adjacent the neck of the user in fluid communication with the air flow guide channel, the air flow guide channel fluidly connecting the air intake to the air flow outlet; and a blower received in the air flow guide channel and configured to draw air into the air flow guide channel through the air intake and to blow the air vertically through the air flow guide channel and out the air flow outlet thereby providing convective cooling of at least one of the neck and a head of the wearer;

wherein the blower comprises a fan enclosure defining an interior chamber and at least one at least one fan received in the interior chamber of the fan enclosure; and wherein the fan enclosure has a curved end.

14. A ventilated garment as set forth in claim 13 further comprising a lumbar support cushion operatively aligned with the curved end of the fan enclosure for being pressed against a lumbar region of the back of the wearer by the curved end of the fan enclosure when the ventilated garment is worn by the wearer and the back of the wearer is supported against a support surface.

15. A ventilated garment configured to be supported on a back of a wearer, the ventilated garment comprising:

a panel having a top edge margin and an opposite bottom edge margin, the panel being shaped and arranged for extending vertically along the back of the wearer when the ventilated garment is supported on the back of the wearer such that the bottom edge margin is positioned adjacent a lumbar region of the back and the top edge margin is positioned adjacent a neck of the wearer; and a blower connected to the ventilated garment adjacent the bottom edge margin of the panel configured for blowing air vertically along the panel toward to the top edge margin to provide cooling to the wearer, the blower comprising a curved end arranged for supporting the lumbar region of the wearer when the ventilated garment is worn by the wearer and the back of the wearer is supported against a support surface; and a support cushion connected to the ventilated garment for being received between the curved end of the blower and the lumbar region of the wearer when the ventilated garment is worn by the wearer.

16. A ventilated garment as set forth in claim 15 further comprising a pouch attached to the panel adjacent the bottom edge margin thereof, the support cushion being received in the pouch.

17. A ventilated garment as set forth in claim 15 wherein the curved end comprises a downstream end of the blower.

* * * * *